United States Patent
Fogg et al.

(10) Patent No.: US 9,111,144 B2
(45) Date of Patent: Aug. 18, 2015

(54) EYE COLOR PATERNITY TEST

(75) Inventors: Douglas R. Fogg, Sandy, UT (US);
Steven J. Smith, Mendon, UT (US);
Katrina R. Miller, Murray, UT (US);
Adam R. Mansfield, Salt Lake City, UT (US)

(73) Assignee: Identigene, L.L.C., Salt Lake City, UT (US)

( * ) Notice: Subject to any disclaimer, the term of this patent is extended or adjusted under 35 U.S.C. 154(b) by 962 days.

(21) Appl. No.: 13/233,331

(22) Filed: Sep. 15, 2011

(65) Prior Publication Data

US 2013/0070982 A1    Mar. 21, 2013

(51) Int. Cl.
*G06K 9/00* (2006.01)
*G06K 9/46* (2006.01)
*A61B 3/00* (2006.01)

(52) U.S. Cl.
CPC .......... *G06K 9/00617* (2013.01); *G06K 9/4609* (2013.01); *A61B 3/0025* (2013.01); *G06T 2207/30041* (2013.01)

(58) Field of Classification Search
CPC ... G06K 9/00617; G06K 9/46; G06K 9/4609; G06K 9/4652; G06T 7/408; G06T 11/001; G06T 2207/30041; A61B 3/0025
See application file for complete search history.

(56) References Cited

U.S. PATENT DOCUMENTS

| | | | |
|---|---|---|---|
| 5,432,863 A | | 7/1995 | Benati et al. |
| 5,850,463 A | * | 12/1998 | Horii ............................ 382/118 |
| 5,990,973 A | | 11/1999 | Sakamoto |
| 6,728,401 B1 | | 4/2004 | Hardeberg |
| 6,925,205 B2 | * | 8/2005 | Leedham et al. ............. 382/167 |
| 7,574,016 B2 | * | 8/2009 | Steinberg et al. ............ 382/103 |
| 7,640,113 B2 | * | 12/2009 | Frudakis et al. ................ 702/19 |
| 7,675,652 B2 | | 3/2010 | Demandolx et al. |
| 7,760,917 B2 | * | 7/2010 | Vanhoucke et al. .......... 382/115 |
| 7,788,188 B2 | * | 8/2010 | Kramer ......................... 705/319 |
| 7,804,983 B2 | * | 9/2010 | Steinberg et al. ............ 382/118 |
| 7,959,295 B2 | * | 6/2011 | Richards et al. ................. 353/7 |
| 8,024,128 B2 | * | 9/2011 | Rabinowitz et al. ........... 702/19 |
| 8,213,737 B2 | * | 7/2012 | Steinberg et al. ............ 382/275 |
| 8,311,289 B2 | * | 11/2012 | Vanhoucke et al. .......... 382/115 |
| 8,389,485 B2 | * | 3/2013 | Czech et al. ................ 514/44 A |
| 8,612,397 B2 | * | 12/2013 | Henderson .................... 707/687 |
| 8,617,812 B2 | * | 12/2013 | Richt ............................ 435/6.1 |

(Continued)

OTHER PUBLICATIONS

Eye Color Calculator—Web application available at: http://museum.thetech.org/ugenetics/eyeCalc/eyecalculator.html, visited on Sep. 15, 2011.

(Continued)

*Primary Examiner* — Manav Seth
(74) *Attorney, Agent, or Firm* — TraskBritt, P.C.

(57) ABSTRACT

A method, system, and apparatus for determining paternity based on eye color. Determining paternity may include accessing a color digital image of at least one of a male parental candidate, a female parental candidate, and a child candidate. An eye color of each of the male parental candidate, the female parental candidate, and the child candidate may be determined, wherein the eye color of at least one of the male parental candidate, the female parental candidate, and the child candidate is determined based on the accessed color digital image. A paternity likelihood of the male parental candidate with regard to the child candidate may be determined based on the determined eye color of the male parental candidate, the female parental candidate, and the child candidate.

17 Claims, 9 Drawing Sheets

(56) References Cited

U.S. PATENT DOCUMENTS

| | | | | |
|---|---|---|---|---|
| 8,631,387 B2* | 1/2014 | Henderson | | 717/108 |
| 8,831,293 B2* | 9/2014 | Wolf et al. | | 382/118 |
| 2002/0188436 A1* | 12/2002 | Schmidt et al. | | 704/1 |
| 2003/0093182 A1* | 5/2003 | Yokoyama | | 700/245 |
| 2003/0211486 A1* | 11/2003 | Frudakis | | 435/6 |
| 2006/0052945 A1* | 3/2006 | Rabinowitz et al. | | 702/20 |
| 2007/0020651 A1* | 1/2007 | Frudakis | | 435/6 |
| 2008/0154566 A1* | 6/2008 | Myres et al. | | 703/11 |
| 2008/0163824 A1* | 7/2008 | Moser et al. | | 119/174 |
| 2009/0183122 A1* | 7/2009 | Webb et al. | | 715/840 |
| 2009/0274368 A1* | 11/2009 | Watanabe | | 382/167 |
| 2010/0271365 A1* | 10/2010 | Smith et al. | | 345/419 |
| 2011/0037829 A1* | 2/2011 | Hata | | 348/43 |
| 2011/0104669 A1* | 5/2011 | Kayser et al. | | 435/6 |
| 2013/0136319 A1* | 5/2013 | Vanhoucke et al. | | 382/118 |
| 2014/0335047 A1* | 11/2014 | Ostroff | | 424/85.2 |

OTHER PUBLICATIONS

MB Eye color Inheritence 1.10—Can be downloaded at: http://download.cnet.com/MB-Eye-Color-Inheritance/3000-2132_4-10865107.html, visited on Sep. 15, 2011.

Eye Color Paternity Test—Web application available at: http://www.dnatesting.com/resources/eye-color-paternity-test.php. visited on Sep. 15, 2011.

* cited by examiner

EYE COLOR PATERNITY TEST

TECHNICAL FIELD

Embodiments of the present disclosure relate to paternity testing and more particularly relate to determining paternity based on eye color and the use of digital imaging to determine eye color.

BACKGROUND

Paternity testing is used to determine whether two individuals have a parent-child relationship. Today, accurate paternity testing utilizes modern genetic analysis techniques based on DNA. Previously, other types of paternity testing have been performed based on physical characteristics such as eye color and blood type. Even though such testing based on physical characteristics is typically not as accurate as modern genetic testing, such tests may still be used to provide preliminary results before a more accurate genetic test is performed.

For example, conventional testing methods based on eye color may include comparing the eye color of a candidate mother, father, and child to determine whether the eye color of the mother and father could have resulted in the eye color of the child. However, such tests are often inaccurate because eye color often appears much lighter at birth and may not darken to its true color for several years. Furthermore, natural variations in human genes may also influence eye color. Thus, even though an eye color paternity test may offer some clues about paternity, it is not typically consistent enough for definitive paternity test results. Nevertheless, eye color paternity testing may still be useful as a preliminary test to encourage more accurate genetic testing. Furthermore, eye color paternity testing has value as a novelty tool for parents wondering about the paternity of a child.

Some conventional eye color paternity tests can be performed quickly using a programmed electronic computing device. However, conventional devices rely on a user to input the eye color of the mother, father, and child into the device. This often results in inaccurate eye color determinations and subsequently inaccurate paternity results. Conventional devices fail to utilize actual digital images of candidate parents and children to more accurately determine eye color. Furthermore, conventional devices lack the entertainment value of capturing and comparing actual images of the physical characteristics of candidate parents and children. Such devices also lack the ability to provide advertisements and/or information to a user about additional testing and where to obtain additional paternity test products and services.

SUMMARY OF INVENTION

There is a need in the art for a device that enables a user to quickly determine eye color based on a digital image and to perform a preliminary paternity test based on the determined eye color. Furthermore, a device is needed that is configured to provide advertisements and additional information to a user regarding where and how to obtain more accurate paternity testing. A method, system, and apparatus are provided herein for determining likelihood of paternity based on eye color.

The method may include accessing a color digital image of at least one of a male parental candidate, a female parental candidate, and a child candidate. The method may further include determining an eye color of each of the male parental candidate, the female parental candidate, and the child candidate, wherein the eye color of at least one of the male parental candidate, the female parental candidate, and the child candidate is determined based on the accessed color digital image. The method may also include determining a paternity likelihood of the male parental candidate and the female parental candidate with regard to the child candidate based on the determined eye color of the male parental candidate, the female parental candidate, and the child candidate.

In one embodiment, the method includes accessing a color digital image of at least one of the male parental candidate, the female parental candidate, and the child candidate. In a further embodiment, the method includes the eye color of each of the male parental candidate, the female parental candidate, and the child candidate and is determined based on the accessed color digital image of each of the male parental candidate, the female parental candidate, and the child candidate respectively. In some embodiments, the eye color of the at least one of the male parental candidate, the female parental candidate, and the child candidate is determined by comparing the color digital image to a set of predefined human eye colors. In a further embodiment, the eye color of the at least one of the male parental candidate, the female parental candidate, and the child candidate is selected by a user from the set of predefined human eye colors. In yet a further embodiment, a user may be prompted with a proposed color from the set of predefined human eye colors in response to selection of a portion of the color digital image with an input device.

In some instances, the eye color of the at least one of a male parental candidate, a female parental candidate, and a child candidate is determined automatically. The eye color of the at least one of a male parental candidate, a female parental candidate, and a child candidate is determined automatically based on a comparison of a color of one or more pixels of the color digital image with the set of human eye colors. In a further embodiment, the eye color of the at least one of a male parental candidate, a female parental candidate, and a child candidate is determined automatically based on a comparison of a color of a plurality of pixels of the color digital image with the set of human eye colors. In yet another embodiment, the eye color of the at least one of a male parental candidate, a female parental candidate, and a child candidate is determined by averaging a plurality of pixel colors of the color digital image to determine an average eye color based on the color digital image Determining the eye color of the eye of the at least one parental candidate may include displaying the captured digital image of the eye of the at least one parental candidate on an electronic display; receiving input from a user to select a portion of the digital image that represents the eye color of the eye of the at least one parental candidate; and selecting a color that best matches the color of the selected portion of the digital image. In a further embodiment, the eye color of the at least one parental candidate is determined by averaging a plurality of colors of the color digital image to determine an average eye color based on the color digital image.

In one embodiment, the method includes displaying the captured color digital image of the eye of the at least one parental candidate on an electronic display; receiving input from a user to select a portion of the digital image that represents the eye color of the eye of the at least one of the male parental candidate, the female parental candidate, and the child candidate; and selecting a color that best matches the color of the selected portion of the digital image. The method may also include displaying an advertisement for additional paternity testing and determining a location nearest to a user where additional paternity testing may be obtained. In some embodiments, the method includes capturing the digital image of the at least one parental candidate with a digital imaging device. In a further embodiment, the method includes determining an eye color of one or more candidate grandparents wherein determining a paternity likelihood is at least partially based on the determined eye color of the one or more candidate grandparents. In yet a further embodiment, the method includes determining an eye color of one or more candidate siblings wherein determining a paternity likelihood is at least partially based on the determined eye color of the one or more candidate siblings An electronic device is provided for determining paternity based on eye color that includes a processor, a memory, and a display. The electronic device may further include a digital imaging module, an eye color module, and a paternity module configured to substantially perform the method acts described above. In one embodiment, the digital imaging module, eye color module, and paternity module may be stored on a non-transitory computer readable medium.

DETAILED DESCRIPTION

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In the following detailed description, reference is made to the accompanying drawings, which form a part hereof, and in which is shown, by way of illustration, specific embodiments in which the invention may be practiced. These embodiments are described in sufficient detail to enable a person of ordinary skill in the art to practice the invention. However, other embodiments may be utilized, and structural, logical, and electrical changes may be made without departing from the scope of the invention. The illustrations presented herein are not meant to be actual views of any particular device or system, but are merely idealized representations that are employed to describe embodiments of the present disclosure. The drawings presented herein are not necessarily drawn to scale. Additionally, elements common between drawings may retain the same or have similar numerical designation.

Figure 1:
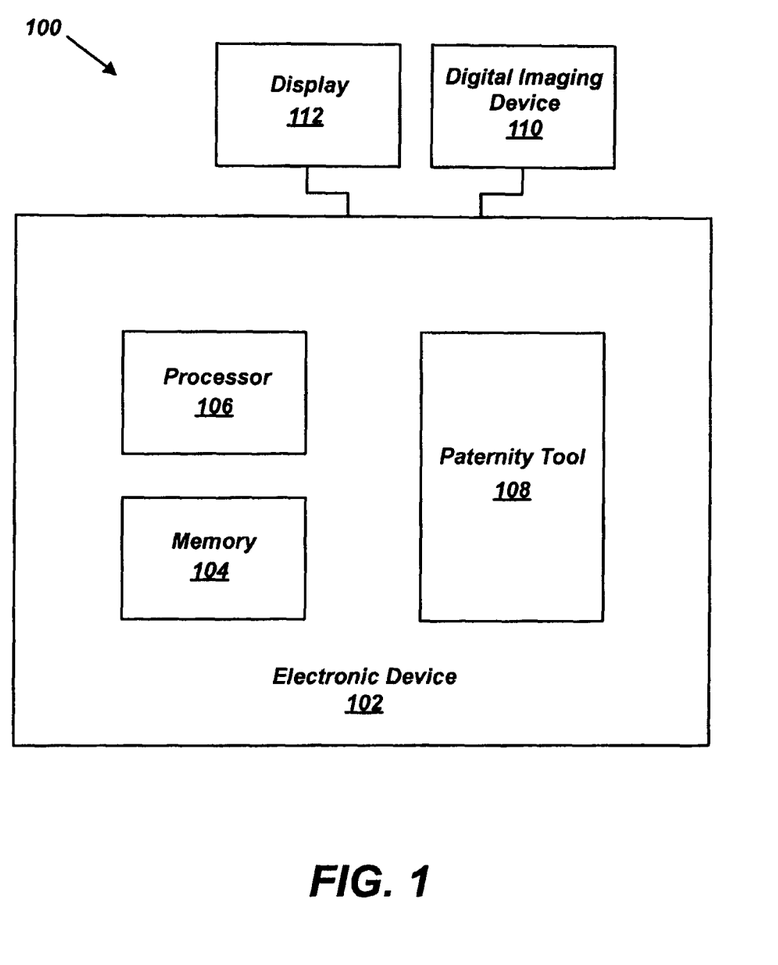
FIG. 1 is a schematic block diagram illustrating one embodiment of a system for performing a paternity test in accordance with the present invention.

FIG. 1 depicts one embodiment of a system 100 for performing a paternity test based on physical characteristics and phenotype information. The system 100 includes an electronic device 102 that includes a memory 104 and a processor 106. As will be recognized by one of skill in the art, the electronic device 102 may be a device such as a personal computer, laptop, client, server, personal digital assistant ("PDA"), cell phone, smart phone, or the like. The electronic device 102 includes a paternity tool 108 that is configured with the logic necessary to perform paternity testing based on physical characteristics such as eye color. Although other physical characteristics may be used in accordance with the paternity tool 108, the present description will focus primarily on eye color. Other characteristics that may be included for analysis include, but are not limited to, ear lobe type, widow's peak type, tongue type, blood type, and other characteristics that are useful in determining paternity. Additionally, although the present description may focus on human characteristics, it is contemplated that the physical characteristics of other animal types may be used in accordance with the present device. For example, a dog breeder may use an embodiment of the tool described herein to analyze the paternity of a puppy.

In various embodiments, the paternity tool 108 may be installed on the electronic device 102, accessed on an external device such as on a web server, stored on a computer readable medium, or may be implemented on the electronic device 102 using other computer processing techniques known in the art. Generally, the paternity tool 108 is configured to perform the logic necessary to utilize digital images to determine the eye color of one or more parental candidates and a child candidate, and to make paternity determinations based on the eye color determined from the digital images. Preferably, color digital images are used in accordance with the present invention, but other types of digital images are contemplated if they include sufficient data for determining the eye color of a subject depicted in the digital image. For example, the user may capture a digital image of a candidate mother, candidate father, and/or a candidate child, and the paternity tool 108 may be used to determine the eye color of each of the candidate mother, candidate father, and candidate child. Once the eye color of the candidate mother, candidate father, and candidate child is determined, the paternity tool 108 may determine whether the candidate child is potentially the biological offspring of the candidate mother and the candidate father. The paternity tool 108 may then present the results to a user and display an advertisement or instructions on how to obtain a more accurate paternity test. The paternity tool 108 provides a preliminary paternity test and may be used simply for entertainment purposes in some instances.

In one embodiment, the system 100 includes a digital imaging device 110 such as a digital camera, web-cam, digital video camera, or the like. The digital imaging device 110 may be utilized to capture digital images of candidate parents and/or candidate children. As will be recognized by one of skill in the art, the digital imaging device 110 may be integrated into a device such as a cell phone or PDA. In the case where a portable device such as a PDA or cell phone is used, the paternity tool 108 may be implemented as an application or "app" installed on the device. Such an implementation enables for the paternity tool 108 to be portable and readily available to a user on the go. Furthermore, the electronic device 102 may be configured to access the Internet or to communicate wirelessly with other devices such as through a Wi-Fi or other communication means. Thus, additional information may be retrieved by the paternity tool 108 from remote locations. Such information may include, for example, stored digital images, advertisements, or directions to a distributor that sells additional paternity tests. As depicted, the system 100 may also include a display 112 for displaying graphics, data, images, and the like to the user.

Figure 2A:
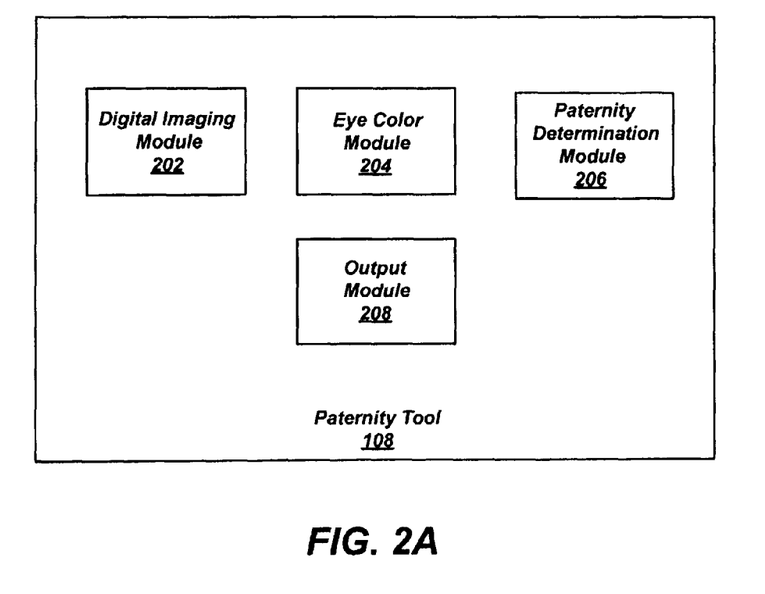
FIG. 2A is a schematic block diagram illustrating one embodiment of a paternity tool for performing a paternity test in accordance with the present invention and FIG. 2B depicts a spectrum of lighter to darker eye colors associated with humans.

FIG. 2 depicts one embodiment of the paternity tool 108 that includes a plurality of logic modules. In the depicted embodiment, the paternity tool 108 includes a digital imaging module 202, an eye color module 204, a paternity determination module 206, and an output module 208. Of course, in other embodiments the paternity tool 108 may include one or more additional modules, and/or the modules may be divided or combined to enable operation of the paternity tool 108.

In the depicted embodiment, the digital imaging module 202 may be configured to access a digital image of at least one parental candidate. In one embodiment, the digital image of a parental candidate may be accessed by first capturing the digital image with a digital imaging device 110 such as a digital camera. In another embodiment, the digital image of the parental candidate may be accessed by retrieving a previously stored digital image of the parental candidate from a storage device. For example, the digital image of the parental candidate may be retrieved by accessing system memory, downloading the image from the interne, receiving the image via email, or by similar means recognized by those of skill in the art.

In certain embodiments, the digital imaging module 202 accesses digital images of each of a male parental candidate, a female parental candidate, and a child candidate. In some embodiments, the digital imaging module 202 may access digital images for fewer than each of the male parental candidate, female parental candidate and child candidate. For example, a digital image of the male parental candidate may be unavailable, in which case, digital images of the female parental candidate and the child candidate may be accessed, and eye color information for the male parental candidate may be input by a user.

The eye color module 204 may be configured to determine an eye color of one or more of the parental candidates based on the digital image. In one embodiment, the eye color module 204 may display the digital image for user to examine. Cropping, zooming, and other photo manipulation tools may be used to display a portion of the digital image that includes the eye of a candidate parent or child. A set of potential human eye colors may be displayed with the digital image for comparison. Typically, human eye color is classified into eight common color types including light-blue, blue, blue-green, green, hazel, light-brown, brown, and dark brown. However, in some instances eye color may be divided into more or fewer color classifications. For the purposes of this description, a set of eight human eye colors will be described. Thus, in one embodiment, a set of eight human eye colors may be displayed next to a digital image of a parental candidate for comparison with the digital image. The set of eight human eye colors may be presented so as to depict one or both of a name of the eye color and a sample of the eye color. Display of a sample of each eye color enables easier comparison with the digital image.

In one embodiment, a user may select the eye color of a candidate parent from the set of colors that most closely matches the color in the digital image. In another embodiment, digital processing may be implemented to automatically detect an eye color from the digital image and match it to a color from the set of eye colors. In one embodiment, an input device such as a touch screen, mouse, or other device, may be used to select the portion of the digital image that depicts the iris, the part of the eye that is associated with eye color. For example, a cursor may be directed over the digital image so as to select one or more pixels that depict the color of an eye from the digital image. The eye color module 204 may suggest a matching eye color for the selected portion of the iris as the cursor is moved over different portions of the digital image. For example, as a cursor is moved over a certain colored pixel or group of pixels, a pop-up box or other display mechanism may be presented to a user that suggests a color match for the pixel or group of pixels. In this manner a user may determine a color from the set of eight eye colors that most closely matches the iris color from the digital image.

In at least one embodiment, the eye color of the parental or child candidate may be determined by averaging a plurality of pixel colors of the color digital image to determine an average eye color based on the color digital image. For example, a user may use a cursor to select several sample pixel colors from the digital image (e.g. several samples from the iris portion of the color digital image). The several sample pixel colors may be averaged together to determine an average eye color and/or to suggest an average color for selection by a user. In at least one embodiment, selecting sample colors may include using an input device to click (e.g. with a mouse) or tap (e.g. with a touchscreen) on various parts of the eye depicted in the color digital image to select corresponding pixel colors for averaging. In some instances, the eye color depicted in the digital image may not be uniform across the iris, and in such instances averaging a sample of multiple selected eye colors may improve accuracy of the test.

In a further embodiment, an input device may be used to select the portion of the digital image that represents eye color by encircling, cropping, selecting, and/or otherwise indicating the iris portion of the color digital image. Digital processing may then be used to determine an average color of all of the colors (e.g. each pixel color) in the selected portion of the digital image to determine an average eye color. For example, each pixel in the selected portion of the color digital image may be examined to determine a color of the pixel and ultimately to determine an average eye color for the candidate depicted in the color digital image.

In yet a further embodiment, a predetermined number of samples of pixel colors from the encircled portion of the digital image may be used to determine the average eye color, such that each pixel need not be examined. In some instances, the predetermined number of samples may correspond to predetermined locations of the eye of the candidate parent or child. For example, the eye color module 204 may be configured to select samples from the inner part of the iris, the outer part of the iris, the middle of the iris, in a uniform pattern across the iris, etc. In at least one embodiment, the eye color module 204 may automatically detect a plurality of sample pixel colors from the digital image and automatically combine them to determine an eye color of the person depicted in the color digital image or to suggest an eye color for selection by a user. In some embodiments, the eye color module 204 may be configurable with settings that allow a user to select a type of color identification methodology, such as using a single color sample, using multiple color samples, using all pixels in a selected portion of the digital image, automatically selecting an eye color, presenting a proposed eye color to a user, or the like.

In at least one embodiment, the electronic device 102 and/or its display 112 may be calibrated to ensure a more accurate color match. For example, conventional displays 112 may have settings such as color, brightness, and contrast that allow for the appearance of the display to be adjusted. The display 112 may be adjusted accordingly to ensure that the colors are being accurately displayed. Furthermore, the digital imaging device 110 may be used to further calibrate the display 112 by capturing images of known colors and ensuring that they are properly displayed on the display 112 of the electronic device. In some instances, capturing the digital images of the candidate parents and candidate child with the same digital imaging device 110 may result in more accurate eye color determinations by eliminating display differences that may result from disparate digital imaging devices.

Figure 2B:
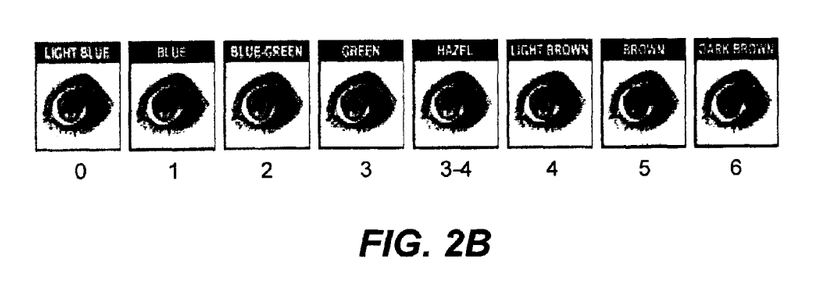

Once eye color information for each of the candidate parents and the candidate child is determined, the paternity determination module 206 determines whether the selected eye color for the parental candidates, if they mated, could result in the eye color of the child candidate. This determination is made based on known eye color inheritance patterns as will be recognized by one of skill in the art. Generally, an eye color paternity test assumes that light-eyed parents cannot have darker-eyed children. FIG. 2B depicts a spectrum of lighter to darker eye colors associated with humans.

Eye color follows a polygenic inheritance pattern. Generally, these genes express themselves as one of the eight depicted eye colors. "Dark" is dominant in the genes that determine eye color, and the more dominant alleles present, the darker eye color appears. From this information, the paternity determination module 206 makes a reasoned predication regarding the likelihood of paternity based on the known eye colors of the parental candidates and child candidates. Generally, two "light-blue" eyed parents cannot have a "blue" eyed (or darker eyed) child. Two "blue" eyed parents can have a "blue-green" (or lighter) eyed child, but not hazel or anything darker. Two "blue-green" eyed parents can have a "light-brown" (or lighter) eyed child, but not brown or anything darker. One "light-brown" eyed parent and one "blue-green" eyed parent can have a child with any of the possible eye colors. Two "dark-brown or black" eyed parents can have a child any of the possible eye colors (but it is unlikely that they will have a light eyed child, such as a light blue or blue).

The output module 208 outputs the results of the paternity determination, such as by displaying "match", signifying possible paternity, or "no match", signifying that paternity is not likely based on the eye color analysis. The output module 208 may also display advertisements for and provide instructions on how to obtain a more accurate paternity test. Additional information may also be presented to the user such as information about how eye color genetics work and the eye color of the parents and child may not be consistent with a biological relationship. In one embodiment, a link may be provided to an information page further explaining the eye color test and the results. In further embodiments, the output module 208 may display a potential range of eye color for a child based on the eye color of the two candidate parents. For example, if the first candidate parent has light-brown eyes and the second candidate parent has blue-green eyes, the output module 208 may display information explaining that a potential child may have any of the possible eye colors.

FIGS. 3-8 depict simplified top views of an electronic device 302 configured to perform paternity testing based on eye color in accordance with the present invention. Each of FIGS. 3-8 depict examples of what might be displayed by the electronic device 302 during operation of the paternity tool 108 as implemented on the electronic device 302.

Figure 3:
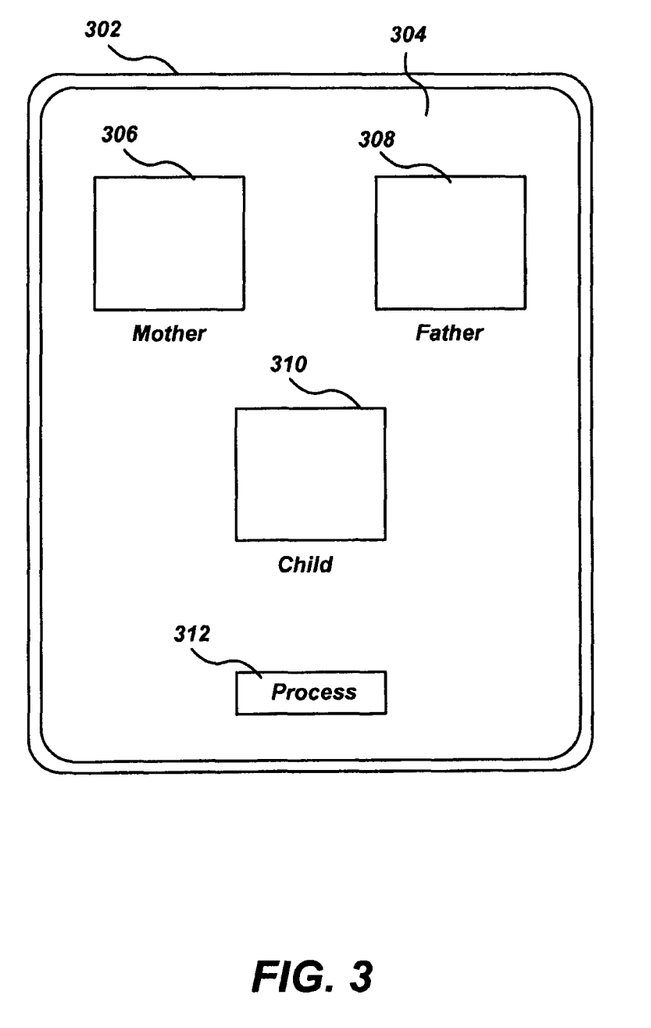
FIG. 3 is a simplified top view illustrating one embodiment of an electronic device configured to perform paternity testing in accordance with the present invention.

FIG. 3 is a simplified top view illustrating one embodiment of the electronic device 302 configured to perform paternity testing in accordance with the present invention. The electronic device 302 as depicted includes a touch screen display 304 that is configured to receive input from a user based on the location and manner in which the touch screen display 304 is contacted by a user. The touch screen display 304 in FIG. 3 depicts prompts for accessing a digital image of a candidate mother 306, a candidate father 308, and a candidate child 310. A "process" button 312 is also depicted that initiates processing of the paternity test once an eye color for each of the candidate mother 306, candidate father 308, and candidate child 310 have been determined. In one embodiment, touching the candidate mother 306 portion of the touch screen 304 results in a prompt to access a digital image of a candidate mother as depicted in FIG. 4.

Figure 4:
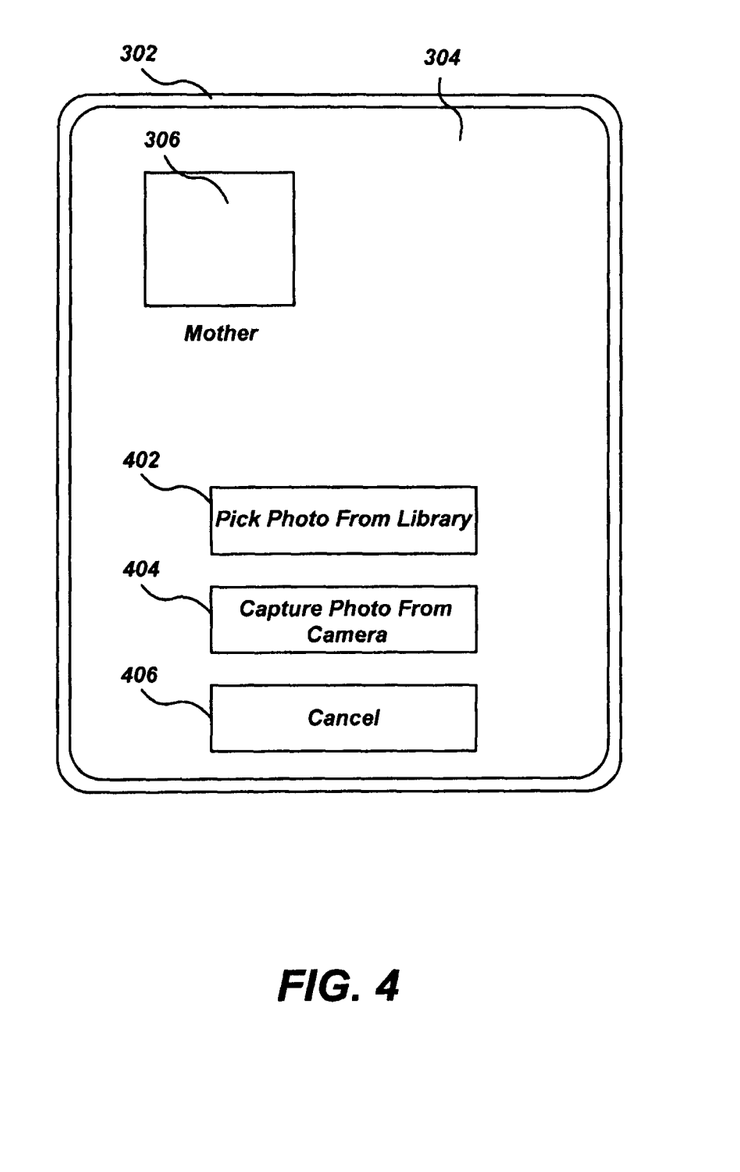
FIG. 4 is a simplified top view further illustrating one embodiment of an electronic device configured to access a digital image in accordance with the present invention.

In response to selecting the candidate mother 306 portion of the touch screen 304, FIG. 4 depicts a display that includes buttons for picking a photo from a library 402, capturing a photo from a camera 404, or canceling the operation 406. From this display, a user may opt to access a photo of the candidate mother that has already been stored, or to use an attached digital imaging device 310 to capture a photo of the candidate mother. If a user initiates the button to pick a photo from a library 402, a screen will be presented to allow a user to navigate to a location of the photo. If a user initiates the button to capture a photo from a camera 404, the attached digital imaging device 310 will be initiated. In one embodiment, the touch screen display 304 may display a camera view when the digital imaging device 110 is initiated. The digital imaging device 110 may then be used to capture images of the candidate parents and/or candidate child. If a user initiates the cancel button 406, the operation is ended.

Figure 5:
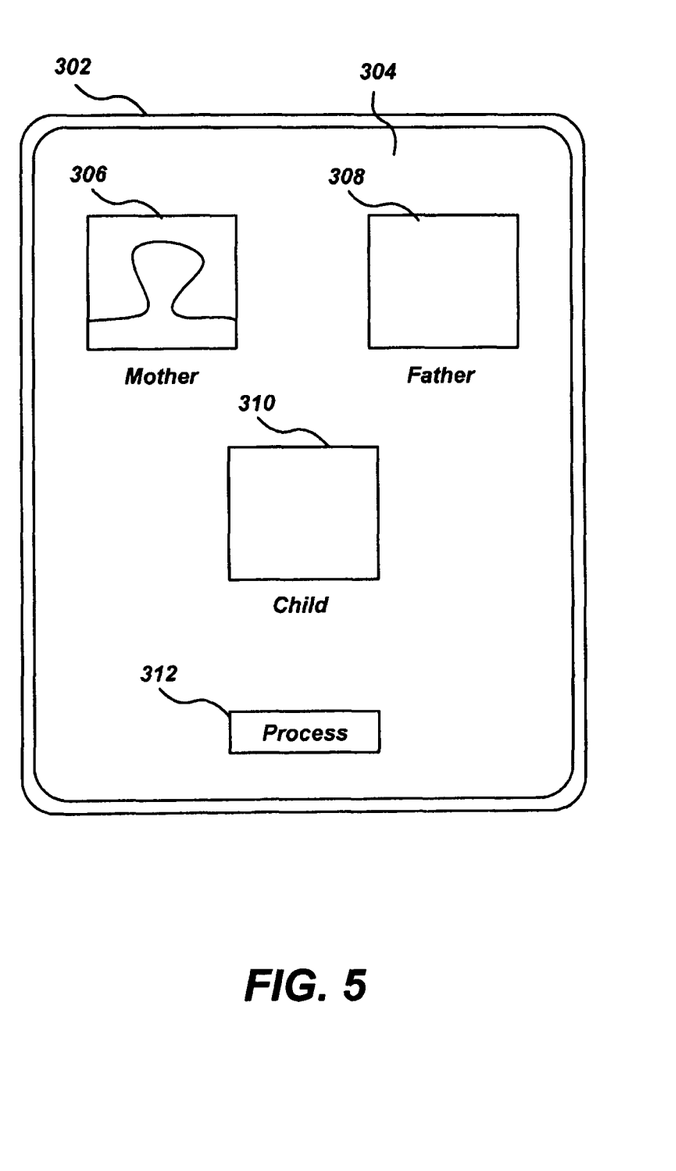
FIG. 5 is a simplified top view further illustrating one embodiment of an electronic device configured to perform paternity testing in accordance with the present invention.

As depicted in FIG. 5, once a digital image is accessed either by retrieving the digital image from a storage location or by capturing a new digital image with a digital imaging device 110, the image is displayed in the candidate mother location of the touch screen display 304. Once a digital image of the candidate mother 306 is retrieved, a digital image for the candidate father 308 and candidate child 310 may be accessed in a similar manner. Of course, the digital images for the candidate mother 306, candidate father 308, and candidate child 310 may be accessed in any order as preferred by the user.

In some instances, multiple candidate parents and children may be considered. For example, if two candidate fathers are available, a digital image of each of the candidate fathers may be accessed and used in the paternity test. In such an embodiment, the paternity test may indicate a preliminary paternity test result for each of the considered fathers. Similarly, the paternity tool 108 may be configured to consider multiple candidate children and/or multiple candidate mothers.

Figure 6:
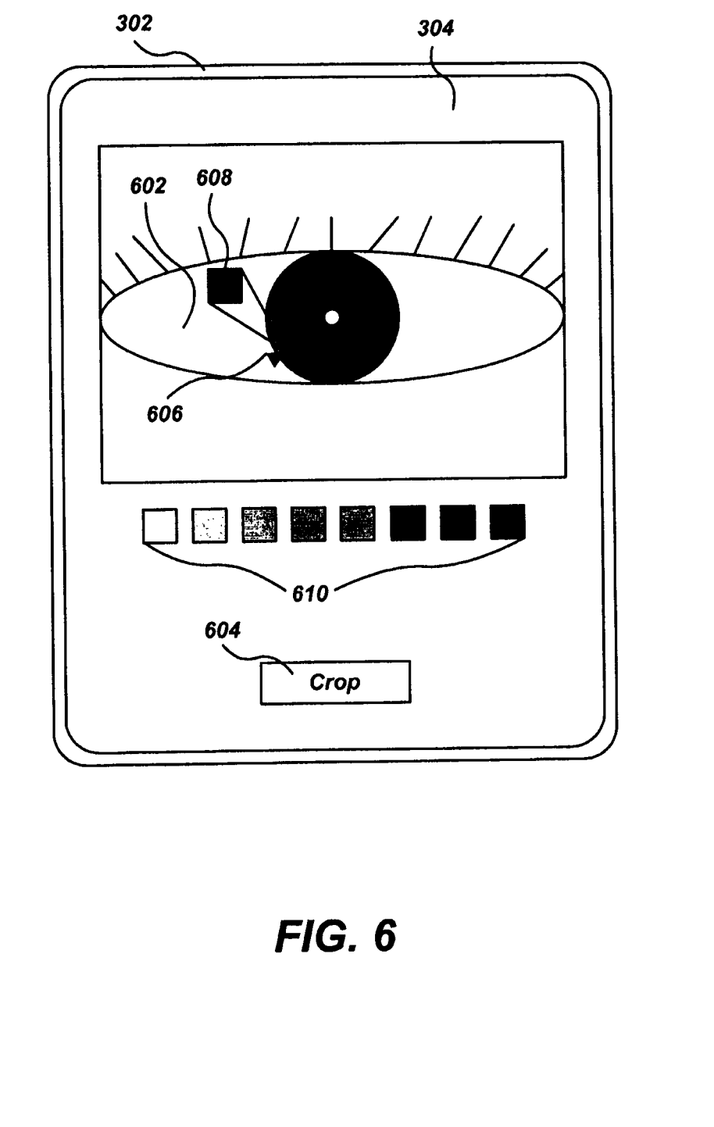
FIG. 6 is a simplified top view further illustrating one embodiment of an electronic device configured to determine an eye color from a digital image in accordance with the present invention.

Once a digital image is obtained, the electronic device 302 may be configured with the logic to manipulate the digital image to better determine the physical characteristics of the candidate parent or child depicted in the digital image. For example, as depicted in FIG. 6, a user may use touch screen controls to zoom in on the eye portion 602 of the digital image. In the depicted embodiment, a crop button 604 may be used to crop the picture around the eye portion 602. In further embodiments, additional image manipulating functions may be incorporated such as rotating the image, reversing the image, or the like. As depicted, a user may manipulate a cursor 606 to select the iris portion of the eye 602 that represents eye color. In one embodiment, as the cursor moves over the digital image, a suggested color 608 may be displayed for examination by a user. The suggested color 608 may represent the color of the current selected pixel or group of pixels. In a further embodiment, the suggested color 608 may represent a closest match to a color from a set of possible human eye colors 610. Based on the eye color from the digital image, a best matching color from the set of possible human eye colors 610 is selected. This may be done by user selection based on a comparison of the digital image with the set of human eye colors 610, or may be performed automatically by the paternity tool 108 using digital processing techniques.

In one embodiment, the paternity tool 108 may take a sampling of a plurality of pixels from the eye portion 602 of the digital image to determine the likely eye color of the candidate parent or candidate child being examined. For example, the paternity tool 108 may determine an average color based on a sampling of many pixels from the iris portion of the digital image. In a further embodiment, it is contemplated that the paternity tool 108 may automatically detect an eye portion of a digital image and determine a closest matching eye color for the detected eye portion of the digital image without substantial input from a user.

Figure 7:
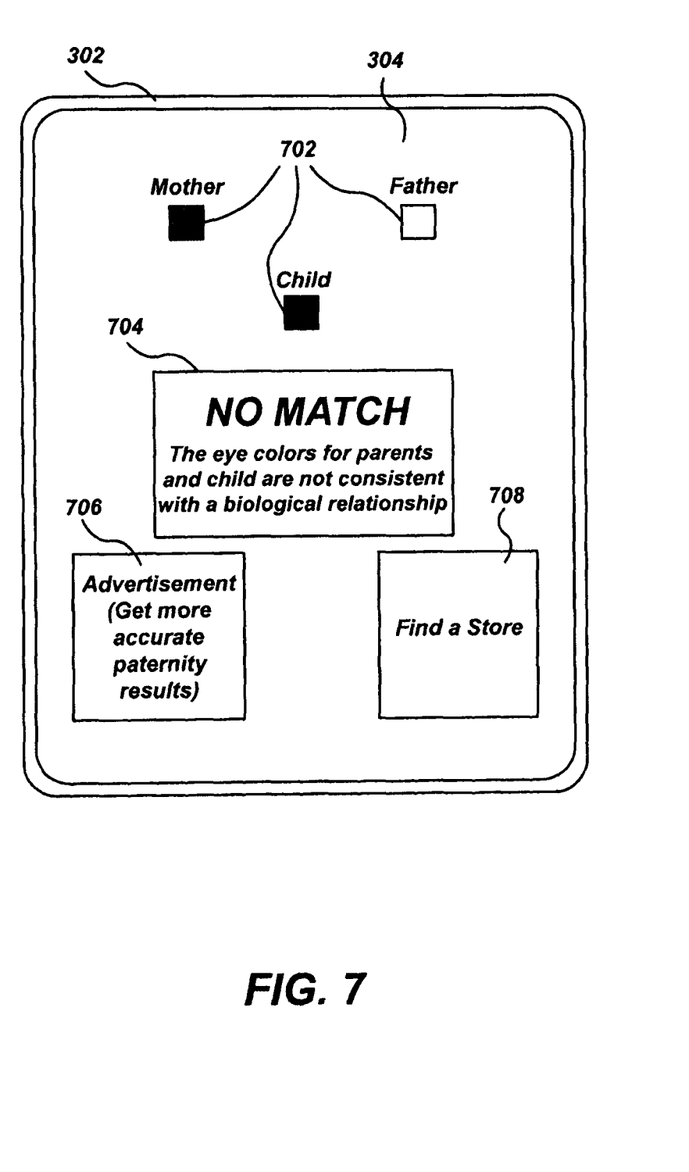
FIG. 7 is a simplified top view further illustrating one embodiment of an electronic device configured to display paternity test results.

Referring to FIG. 5, once an eye color is determined for each of a candidate mother, a candidate father, and a candidate child, a user may initiate the process button 312. In response the electronic device 302 performs operations to determine a paternity result of the candidate child based on the determined eye color of each of the candidate mother, father, and child. FIG. 7 depicts one example of a display of the results of the paternity test. In the depicted embodiment, the selected eye color 702 for each of the candidate parents and the child are depicted, and a result 704 is presented that indicates "NO MATCH." No match, in this case, means that the eye colors selected for the candidate parents are not consistent with a biological relationship with the candidate child. In further embodiments, additional results may be presented including, but not limited to, a listing of potential eye colors for a child of the candidate mother and candidate father and a likelihood of paternity based on the selected eye colors. In further embodiments, the results may incorporate additional information based on other characteristics of the candidate parents and candidate child such as ear lobe type, widows peak type, tongue shape type, blood type, etc. Furthermore, the paternity tool 108 may be configured to prompt the input of such information for each candidate parent and/or child in a manner similar to eye color. In some instances, a digital image may be used to identify additional physical characteristics such as ear lobe type for a candidate parent or child. This information may be used to provide more accurate paternity test results.

As depicted in FIG. 7, an advertisement 706 for a company that provides additional and/or more accurate paternity testing products may be provided. Thus, the paternity tool 108 may be used to initiate target marketing and advertising for paternity testing companies. The paternity tool 108 may also include a link 708 to "find a store" that carries paternity testing products. In one embodiment, selecting the "find a store" button 708 may cause the electronic device 302 to present a list of stores that provide paternity test kits or services. Furthermore, the electronic device 302 may be configured to automatically determine a current location of the electronic device 302 using GPS or other means, and may provide directions or a map to a user for locating a particular distributor of paternity testing products and services.

Figure 8:
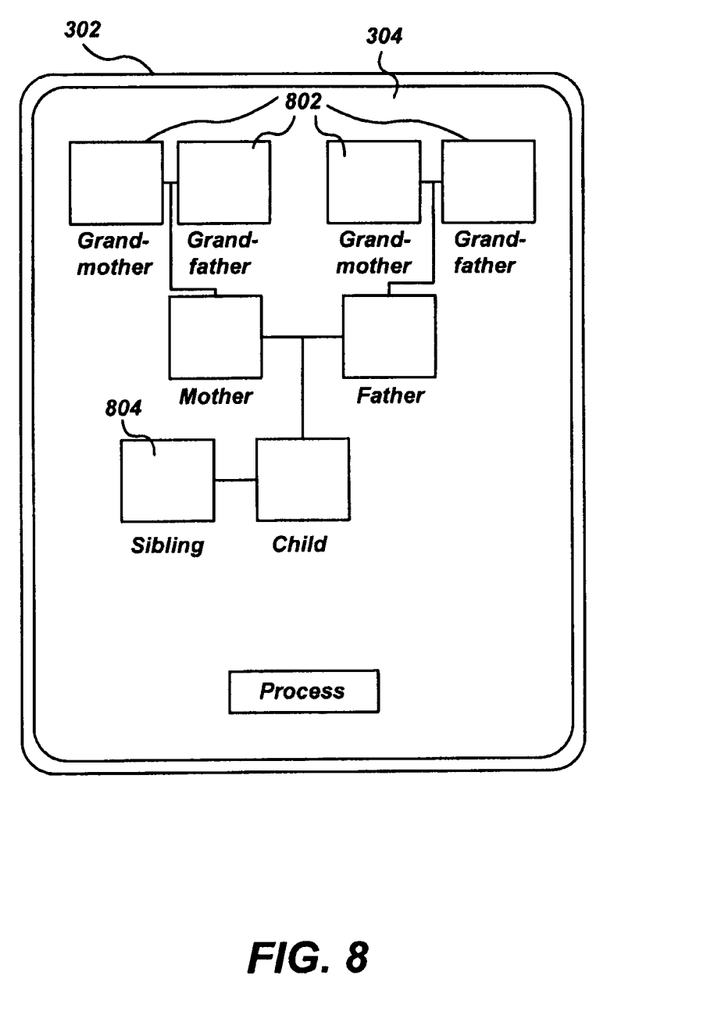
FIG. 8 is a simplified top view further illustrating one embodiment of an electronic device configured to determine paternity by using digital images of grandparents and or siblings in accordance with the present invention.

FIG. 8 is a simplified top view further illustrating one embodiment of an electronic device configured to determine paternity by using digital images of grandparents and or siblings in accordance with the present invention. It is contemplated that in addition to using information about candidate parents and candidate children, the paternity tool 108 may incorporate information about candidate grandparents 802 and candidate siblings 804 of the candidate child. This information may be utilized to provide a more accurate paternity test result. In various embodiments, digital images of candidate grandparents and/or candidate siblings may be utilized to determine physical characteristics such as eye color, ear lobe type, or the like. In further embodiments, where digital images may not be conveniently available, information about candidate grandparents and candidate siblings may be input by a user using conventional means.

Figure 9:
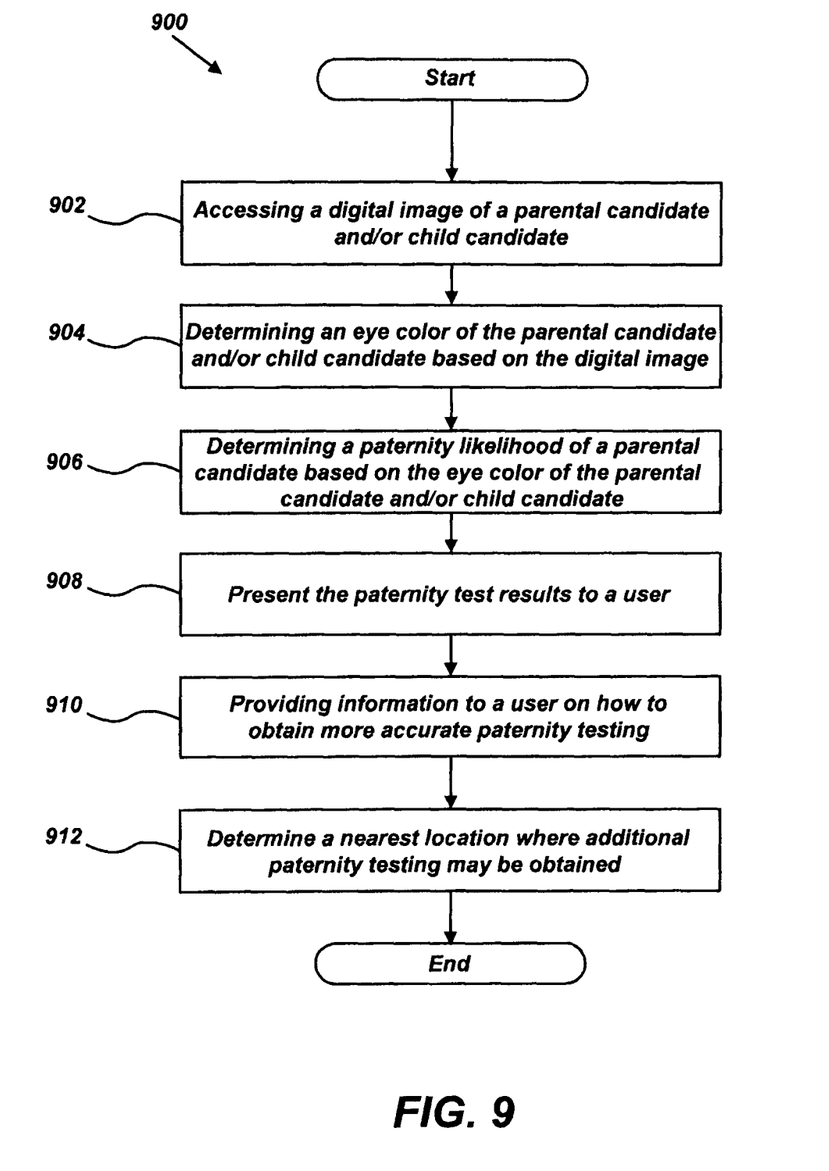
FIG. 9 is a flow chart diagram illustrating one embodiment of a method for performing a paternity test in accordance with the present invention.

FIG. 9 is a flow chart diagram illustrating one embodiment of a method 900 for performing a paternity test in accordance with the present invention. The method 900 substantially includes the embodiments and configurations described above with regard to FIGS. 1-8. The method 900 begins by accessing 902 a digital image of a parental candidate. As explained above, this may be accomplished by accessing a stored image of the parental candidate or by capturing a new digital image of the parental candidate using a digital imaging device 110. From the digital image, an eye color of the parental candidate is determined 904. Photo manipulation tools may be used to zoom in on and crop the eye portion of the digital image. Digital processing techniques may be used to suggest a color of the eye portion of the digital image that corresponds to a known human eye color. In some embodiments, the eye color may be selected automatically using digital image processing performed by an electronic device 102.

A digital image may be accessed and an eye color may be determined for one or more additional candidate parents and/or children. A paternity result is determined 906 for the candidate parents based on the determined eye color of the candidate parents and/or the candidate child. In some embodiments, additional physical characteristics may be included in the paternity analysis to provide a more accurate result. The paternity test results may then be presented 908 to a user via a device such as a display 112, a printout, or other output mechanisms recognized by one of skill in the art.

In some embodiments, information may be provided 910 to a user concerning how to obtain additional paternity testing such as more accurate genetic testing or the like. For example, an advertisement for a genetic testing company or product may be displayed. An electronic device 102 may be used to automatically determine 912 a nearest physical location where addition paternity testing may be obtained. For example, GPS information, a mapping tool, or similar device may be used to direct a user to a location where additional paternity services or products may be obtained. In some embodiments, the method 900 may include additional steps for determining an eye color for candidate grandparents and siblings.

These methods may be practiced in some embodiments with fewer steps or in a different order than are shown. It is thus apparent that a novel and unobvious market analysis method and apparatus has been described in a variety of embodiments. Many additions, deletions, and modifications to the preferred embodiments may be made without departing from the scope of the invention as hereinafter claimed. Further, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of determining paternity based on eye color, the method comprising:
   electronically accessing a color digital image of at least one of a male parental candidate, a female parental candidate, and a child candidate;
   digitally processing the color digital image to determine an eye color of the at least one of the male parental candidate, the female parental candidate, and the child candidate, wherein the eye color of the at least one of the male parental candidate, the female parental candidate, and the child candidate is determined based on the accessed color digital image by comparing a portion of the color digital image to a set of predefined human eye colors;
   determining a paternity likelihood of the male parental candidate and the female parental candidate with regard to the child candidate based on the determined eye color of the at least one of the male parental candidate, the female parental candidate, and the child candidate; and
   displaying the paternity likelihood of the male parental candidate and the female parental candidate with regard to the child candidate on an electronic device.

2. The method of claim 1, further comprising accessing a color digital image of each of the male parental candidate, the female parental candidate, and the child candidate.

3. The method of claim 2, further comprising determining the eye color of each of the male parental candidate, the female parental candidate, and the child candidate based on the accessed color digital image of each of the male parental candidate, the female parental candidate, and the child candidate respectively.

4. The method of claim 1, further comprising determining a set of potential eye colors of the child candidate based on the determined eye colors of the male parental candidate and the female parental candidate.

5. The method of claim 1, wherein the eye color of the at least one of the male parental candidate, the female parental candidate, and the child candidate is selected by a user from the set of predefined human eye colors.

6. The method of claim 5, further comprising prompting the user with a proposed color from the set of predefined human eye colors in response to selection of a portion of the color digital image with an input device.

7. The method of claim 5, wherein the eye color of the at least one of a male parental candidate, a female parental candidate, and a child candidate is determined automatically.

8. The method of claim 7, wherein the eye color of the at least one of a male parental candidate, a female parental candidate, and a child candidate is determined automatically based on a comparison of a color of one or more pixels of the color digital image with the set of human eye colors.

9. The method of claim 7, wherein the eye color of the at least one of a male parental candidate, a female parental candidate, and a child candidate is determined automatically based on a comparison of a color of a plurality of pixels of the color digital image with the set of human eye colors.

10. The method claim 1, wherein the eye color of the at least one of a male parental candidate, a female parental candidate, and a child candidate is determined by averaging a plurality of colors of the color digital image to determine an average eye color based on the color digital image.

11. The method of claim 1, wherein determining the eye color of at least one of the male parental candidate, the female parental candidate, and the child candidate based on the accessed color digital image comprises:
    displaying the captured digital image of the eye of the at least one of the male parental candidate, the female parental candidate, and the child candidate on an electronic display;
    receiving input from a user to select a portion of the digital image that represents the eye color of the eye of the at least one of the male parental candidate, the female parental candidate, and the child candidate; and
    selecting a color that best matches the color of the selected portion of the digital image.

12. A method comprising:
    electronically accessing a color digital image of at least one of a male parental candidate, a female parental candidate, and a child candidate;
    digitally processing the color digital image to determine an eye color of the at least one of the male parental candidate, the female parental candidate, and the child candidate, wherein the eye color of at least one of the male parental candidate, the female parental candidate, and the child candidate is determined based on the accessed color digital image;
    determining a paternity likelihood of the male parental candidate and the female parental candidate with regard to the child candidate based on the determined eye color of the male parental candidate, the female parental candidate, and the child candidate;
    displaying the paternity likelihood of the male parental candidate and the female parental candidate with regard to the child candidate on an electronic device; and displaying an advertisement for additional paternity testing on the electronic device.

13. A method comprising:

electronically accessing a color digital image of at least one of a male parental candidate, a female parental candidate, and a child candidate;

digitally processing the color digital image to determine an eye color of the at least one of the male parental candidate, the female parental candidate, and the child candidate, wherein the eye color of at least one of the male parental candidate, the female parental candidate, and the child candidate is determined based on the accessed color digital image;

determining a paternity likelihood of the male parental candidate and the female parental candidate with regard to the child candidate based on the determined eye color of the male parental candidate, the female parental candidate, and the child candidate;

displaying the paternity likelihood of the male parental candidate and the female parental candidate with regard to the child candidate on an electronic device; and determining a location nearest to a user of the electronic device where additional paternity testing may be obtained.

14. The method of claim 1, further comprising capturing the digital image of at least one of the male parental candidate, the female parental candidate, and the child candidate with a digital imaging device associated with the electronic device.

15. A method of determining paternity based on eye color, the method comprising:

electronically accessing a color digital image of at least one of a male parental candidate, a female parental candidate, and a child candidate;

digitally processing the color digital image to determine an eye color of the at least one of the male parental candidate, the female parental candidate, and the child candidate, wherein the eye color of at least one of the male parental candidate, the female parental candidate, and the child candidate is determined based on the accessed color digital image;

determining an eye color of one or more candidate grandparents; and determining a paternity likelihood of the male parental candidate and the female parental candidate with regard to the child candidate based on the determined eye color of the male parental candidate, the female parental candidate, and the child candidate, wherein determining a paternity likelihood is at least partially based on the determined eye color of the one or more candidate grandparents; and displaying the paternity likelihood of the male parental candidate and the female parental candidate with regard to the child candidate on an electronic device.

16. A method of determining paternity based on eye color, the method comprising:

electronically accessing a color digital image of at least one of a male parental candidate, a female parental candidate, and a child candidate;

digitally processing the color digital image to determine an eye color of the at least one of the male parental candidate, the female parental candidate, and the child candidate, wherein the eye color of at least one of the male parental candidate, the female parental candidate, and the child candidate is determined based on the accessed color digital image;

determining an eye color of one or more candidate siblings;

determining a paternity likelihood of the male parental candidate and the female parental candidate with regard to the child candidate based on the determined eye color of the male parental candidate the female parental candidate, and the child candidate, wherein determining a paternity likelihood is at least partially based on the determined eye color of the one or more candidate siblings; and displaying the paternity likelihood of the male parental candidate and the female parental candidate with regard to the child candidate on an electronic device.

17. A method comprising:

capturing a digital image of an eye of at least one of a male parental candidate, a female parental candidate, and a child candidate with an electronic device selected from the group consisting of cell phones, smart phones, digital cameras, web-cams, and digital video cameras;

displaying the digital image on an electronic display associated with the electronic device;

receiving input from a user to select a portion of the digital image that represents an eye color of the eye of at least one of the male parental candidate, the female parental candidate, and the child candidate;

sampling a plurality of pixels of the digital image;

digitally processing the digital image to determine an eye color of the at least one of the male parental candidate, the female parental candidate, and the child candidate, wherein the eye color of at least one of the male parental candidate, the female parental candidate, and the child candidate is determined based on the plurality of pixels by comparing at least one of the pixels to a set of predefined human eye colors;

determining a paternity likelihood of the male parental candidate and the female parental candidate with regard to the child candidate based on the determined eye color of the male parental candidate, the female parental candidate, and the child candidate; and displaying information about the paternity likelihood on the electronic display.

* * * * *